US010769246B2

(12) United States Patent
Viljoen et al.

(10) Patent No.: US 10,769,246 B2
(45) Date of Patent: Sep. 8, 2020

(54) CUSTOM NUTRITIONAL SUPPLEMENT COMPOSITION PRODUCTION SYSTEM AND METHOD

(71) Applicants: Alwyn Johannes Jacobus Viljoen, Pretoria (ZA); Bernard Etienne Nortje, Pretoria (ZA)

(72) Inventors: Alwyn Johannes Jacobus Viljoen, Pretoria (ZA); Bernard Etienne Nortje, Pretoria (ZA)

(*) Notice: Subject to any disclaimer, the term of this patent is extended or adjusted under 35 U.S.C. 154(b) by 147 days.

(21) Appl. No.: 15/400,428

(22) Filed: Jan. 6, 2017

(65) Prior Publication Data

US 2017/0193193 A1    Jul. 6, 2017

Related U.S. Application Data

(63) Continuation-in-part of application No. PCT/ZA2015/000048, filed on Jul. 7, 2015.

(51) Int. Cl.
*G06Q 30/00* (2012.01)
*G06F 19/00* (2018.01)
(Continued)

(52) U.S. Cl.
CPC ............ *G06F 19/3475* (2013.01); *A23L 5/00* (2016.08); *A23L 27/00* (2016.08); *A23L 33/10* (2016.08); *A23V 2002/00* (2013.01)

(58) Field of Classification Search
CPC .................................................... G06Q 30/00
See application file for complete search history.

(56) References Cited

U.S. PATENT DOCUMENTS 5,087,128 A * 2/1992 Matthews ............. B01F 13/103
366/14
5,895,672 A * 4/1999 Cooper ............... A47J 31/0615
426/433
(Continued)

OTHER PUBLICATIONS

Lab21, https://web.archive.org/web/20030801084917/http://www.lab21.com/new/skinprofiler.htm, Waybackmachine, dated Aug. 1, 2003 (Year: 2003).*

(Continued)

*Primary Examiner* — Mark A Fadok
(74) *Attorney, Agent, or Firm* — Luedeka Neely Group, PC (57) ABSTRACT

The invention provides a system which implements a method of altering the flavour, stability, consistency, texture and colour of the a custom nutritional supplement composition containing nutritional supplement ingredients selected by a user of the system, said method including addition of specific additives in specific quantities to a custom nutritional supplement composition recipe, which additives and quantities are selected through the retrieval of data stored on a computer system which data has correlated the combinations of nutritional supplement ingredients, the additives, and their relative quantities. The system extends to an automated method of preparing a custom nutritional supplement composition, said method including preparing one or more master batches or base mixes and add-mixes including one or more nutritional supplement ingredients and/or one or more additives in predetermined ratios, and in response to a user custom nutritional supplement composition product request, combining calculated or selected quantities of one or more master batches including base mixes and/or add-mixes, one or more additives, and/or one or more nutritional supplement ingredients thereby to obtain a palatable, stabilised, custom nutritional supplement composition product (Continued)

SYSTEM /METHOD FLOW DIAGRAM having a desired flavour, colour and consistency, or any other sensory characteristics, while reducing the number of components required to be blended to achieve same.

16 Claims, 1 Drawing Sheet

(51) Int. Cl.
*A23L 33/10* (2016.01)
*A23L 5/00* (2016.01)
*A23L 27/00* (2016.01)

(56) References Cited

U.S. PATENT DOCUMENTS

| | | | | |
|---|---|---|---|---|
| 6,516,245 | B1* | 2/2003 | Dirksing | A45D 40/00 700/233 |
| 6,669,975 | B1* | 12/2003 | Abene | A23K 40/00 426/2 |
| 7,349,857 | B2* | 3/2008 | Manzo | G06Q 50/22 705/2 |
| 8,249,946 | B2* | 8/2012 | Froseth | G06Q 10/08 416/72 |
| 2002/0004749 | A1* | 1/2002 | Froseth | G06Q 10/08 705/16 |
| 2002/0082745 | A1* | 6/2002 | Wilmott | A61K 8/044 700/233 |
| 2003/0064134 | A1* | 4/2003 | Eastman, III | A23L 7/126 426/72 |
| 2004/0186782 | A1* | 9/2004 | Schydlowsky | G06Q 20/20 705/15 |
| 2005/0136119 | A1* | 6/2005 | Bunick | A61K 9/0095 424/489 |
| 2005/0191386 | A1 | 9/2005 | Adams | |
| 2006/0010038 | A1* | 1/2006 | Schydlowsky | G06Q 20/20 705/16 |
| 2006/0013920 | A1* | 1/2006 | Schydlowsky | G06Q 20/20 426/1 |
| 2007/0254067 | A1* | 11/2007 | Ha | A61K 8/00 424/49 |
| 2008/0004909 | A1 | 1/2008 | Jung et al. | |
| 2008/0220529 | A1* | 9/2008 | Hulme | A01B 79/005 436/39 |
| 2009/0065570 | A1 | 3/2009 | Peters et al. | |
| 2010/0266723 | A1* | 10/2010 | Bralley, III | G06F 19/3475 426/2 |
| 2011/0293790 | A1* | 12/2011 | Ewing | A23L 29/30 426/72 |
| 2014/0279792 | A1* | 9/2014 | Hudson | G06N 5/02 706/46 |
| 2015/0157677 | A1* | 6/2015 | Kat | A61K 36/31 600/35 |
| 2016/0310916 | A1* | 10/2016 | Janders | F16K 5/04 |
| 2017/0156540 | A1* | 6/2017 | Wheatley | B67D 1/0016 |
| 2017/0246602 | A1* | 8/2017 | Dean | B01F 5/0606 |
| 2017/0344950 | A1* | 11/2017 | Dhagumudi | G06Q 10/101 |

OTHER PUBLICATIONS

Chun-Yuen, "Recipe recommendation using ingredient networks", Univerdity of Michigan, dated May 21, 2012. (Year: 2012).*
International Search Authority International Search Report—PCT/ZA2015/000048, dated Mar. 31, 2016.
International Search Authority Written Opinion—PCT/ZA2015/000048, dated Mar. 31, 2016.

* cited by examiner

CUSTOM NUTRITIONAL SUPPLEMENT COMPOSITION PRODUCTION SYSTEM AND METHOD

FIELD OF THE INVENTION

The invention is in the field of nutritional supplement compositions, in particular the invention is in the field of nutritional supplement compositions which are individually specific to the needs of a specific consumer thereof, herein referred to as custom nutritional supplement compositions.

BACKGROUND TO THE INVENTION

The inventors are aware of websites offering consumers the option of ordering individual nutrient substances from a menu and having these shipped to the consumer either pre-blended or for blending by the consumer in ratio's which the consumer chooses thereby to obtain a custom nutritional supplement composition.

A drawback of these and similar methodologies of preparing custom nutritional supplement compositions is that certain combinations are unpalatable and a need exists for a system and method for providing consumers with custom nutritional supplement compositions which contain the desired nutrients in the desired amounts, by ratio, as well as being palatable and even pleasant to consume.

Current practice in the manufacturing of customized nutritional supplements are based on a client specified combination of nutritional ingredients with the option to add a "flavour pack" which contains a standardised mixture of substances with the objective of altering the flavour of the mixture. However, the inventors are aware that it is not possible to produce a standard flavouring mixture which is effective and economical for all possible combinations of nutritional ingredients.

In other instances a "customisation service" is offered in which it is assumed that the recipe is adjusted by skilled human intervention after the client's criteria is received, in which case the process cannot be effectively and efficiently automated without the use of the current invention. The cost and time of each intervention is also saved through this invention.

The prior patent applications related to customized nutritional supplements, pertain to the collection of subjective and/or objective data relating to an individual, and the formulation of a combination of nutritional substances based on this data, with the objective of optimizing the benefit derived from these products in terms of the individual's health or appearance. Other patent applications also include methods and devices for dispensing customized supplements (WO2005069181 A1, US20020082745 A1, WO2013130576 A1).

The invention which is described below has as its object to ameliorate the problems described above and to provide a palatable custom nutritional supplement.

SUMMARY OF THE INVENTION

According to a first aspect of the invention, there is provided a system which implements a method of altering the flavour, stability, consistency, texture, colour and other organoleptic qualities of a custom nutritional supplement composition containing nutritional supplement ingredients selected by a user of the system, said method including addition of specific additives in specific quantities to a custom nutritional supplement composition recipe, which additives and quantities are selected through the retrieval of data stored on a computer system which data has correlated the combinations of nutritional supplement ingredients, the additives, and their relative quantities.

The system includes a computer system including a user interface whereby the user can submit their selection of nutritional supplement composition ingredients, their quantities per serving or ratios, their preferred flavour, and additive type (eg. sweetener type) preferences which data is processed on a CPU of the computer system. The additive data relevant to the custom nutritional supplement composition is automatically calculated by means of a computer algorithm using input data retrieved from a data storage on the computer system and dependent on the user selected parameters, thereby to formulate a recipe including the custom nutritional composition ingredients and additives for execution by an automated system, or manually.

The method of the system may pertain to the way in which the combination and quantities of these additives are determined, making it possible to automate the production of a custom nutritional supplement composition product, with desired flavour, texture and other sensory characteristics. The product produced by this method will typically be superior to what can be achieved using prior art in an automated process.

Thus, the invention may provide a system and method for the automatic formulation of a final recipe for a nutritional powder supplement, based on the criteria specified by the user, who may be the prescriber or consumer thereof, the criteria typically including specified quantities of nutritional ingredients and/or macro nutrients and/or a flavour option and/or an additive type option chosen from a catalogue detailing the available options and quantity ranges.

The catalogue may be displayed on a website in communication with the computer system.

The method may entail the automatic specification of additives, additional to the combination of nutritional ingredients, macro nutrients, and the like, necessary to satisfy the user's nutritional requirements, with the purpose of creating a final recipe that will ensure the palatability, stability, consistency, texture and colour of the product in its final form before ingestion.

The correlation of the combination of additives required, and their quantities is based on the theoretically and empirically determined relationships of these substances with each offered nutritional ingredient and their combinations and with the additives themselves, in the determination of the final product's sensory properties.

These relationships are predetermined and stored on the computer system to permit retrieval thereof thereby to allow the computer assisted automatic formulation of the final recipe once the input criteria are specified.

The method further includes an automatic procedure to determine the serving size, including volume and mass, necessary to meet the specified criteria as well as the adjustment of the recipe to allow the use of standard serving sizes if required.

This method eliminates the need to either have numerous (at least thousands) of recipes to cover all the possible ingredient combinations or the manual formulation of a custom recipe after the criteria have been specified. It also reduces the need for skilled research and development inputs when formulating a custom or new blend.

According to a second aspect of the invention, there is provided an automated method of preparing a custom nutritional supplement composition, said method including:

preparing one or more master batches or base mixes and add-mixes including one or more nutritional supplement ingredients and/or one or more additives in predetermined ratios; and in response to a user custom nutritional supplement composition product request, combining calculated or selected quantities of one or more master batches including base mixes and/or add-mixes, one or more additives, and/or one or more nutritional supplement ingredients thereby to obtain a palatable, so stabilised, custom nutritional supplement composition product having a desired flavour, colour, consistency or any other sensory characteristics while reducing the number of components required to be blended to achieve same.

The terms "master batch" and variants thereof is used to denote a pre-mixed base mixture or add-mixture and thus is considered equivalent to the term "Base Mix" or "Add-Mix" wherever it appears in the specification.

The master batches may include one or more nutritional ingredients which are used in a number of custom nutritional supplement compositions, so that the number of individual ingredients which need to be handled and blended in the production of the product is reduced. These nutritional ingredients may be premixed in preselected ratios.

The master batches may include one or more additive selected from colourant, stabiliser, thickener, flavouring, sweetener, anti-foaming agents, and preservative. However, the master batches may include any additive permissible for such product.

The master batches may be prepared in advance in large quantities and stored in bulk storage, such as silos, whereas the individual ingredients and additives which may be blended with the master batches are stored in smaller quantities.

The blending of the custom nutritional supplement composition product may be automated at least to the extent of determining and dispensing the master batches required for a particular custom nutritional supplement composition product. The automated method may however include the automated determination and dispensing of individual additives and nutritional ingredients required in addition to the master batches.

EXAMPLE OF EMBODIMENTS OF THE INVENTION

The invention will now be described on the basis of a worked example of how a custom nutritional supplement composition is made. Any disclosure below of a broader scope than that of the example as such is intended to augment the Summary of the Invention above.

In the example, a customer selected from the available ingredients a selection of active ingredients and the quantity of each that he or she requires to have. These are shown in rows 9 to 14 of the table below (Table 1).

The customer also specified the product preferences represented by the Base Mix and Add-Mix choices (Table 1: Cell H3 to H6).

TABLE 1

| "Mixing Inputs" Sheet |||||||
| --- | --- | --- | --- | --- | --- | --- |
| CUSTOMER INPUTS |||||||
| Product Name: | Peter's Pre-Workout | | Base Mix Choice: | | | B1 |
| Recipe Code: | Generated: eg. AB231 | | Add-Mix X Choice: | | | X1 |
| | | | Add-Mix Y Choice: | | | Y1 |
| | | | Add-Mix Z Coice: | | | Z1 |
| | Active Ingredient || | Permissible Range (grams) ||| Selected Amount |
| ID | Factory Code | Name | Min | Recommended | Max | (grams) |
| 1 | A1 | ACIDULANT | | | | |
| 2 | B1 | BUFFER | | | | |
| 3 | S1 | SWEETENESS INGREDIENT X | | | | |
| 4 | M1 | MASKING AGENT | | | | |
| 5 | S2 | SALT | | | | |
| 6 | S3 | STABILIZER | | | | |
| 7 | A2 | ANTICAKING AGENT | | | | |
| 8 | M2 | MCT OIL | | | | |
| 9 | C1 | CREATINE | 0.100 g | 2.500 g | 10.000 g | 5.000 |
| 10 | A3 | ARGININE | 0.100 g | 1.000 g | 5.000 g | 1.000 |
| 11 | C2 | CAFFEINE | 0.020 g | 0.050 g | 0.100 g | 0.050 |
| 12 | L1 | L-LEUCINE | 0.100 g | 1.500 g | 5.000 g | 1.500 |
| 13 | L2 | L-ISOLEUCINE | 0.100 g | 1.500 g | 5.000 g | 1.500 |
| 14 | L3 | L-VALINE | 0.100 g | 1.500 g | 5.000 g | 1.500 |

NB. Table is truncated for this example and typically continues downwards

The additives and quantities thereof in rows 1 to 8 are selected through the retrieval of data stored on a computer system which data has correlated the combinations of nutritional supplement ingredients, the additives, and their relative quantities to obtain a palatable product. The mix obtained is shown in Table 2.

TABLE 2

"Mix Info" Sheet 1
MIX INFO

| | | | | QUANTITIES | | | | |
|---|---|---|---|---|---|---|---|---|
| | | | | | System Calculated Additives (Base Mix and Add-Mixes) | | | |
| | | | | | Base/Add-Mix Category: | | | |
| | | | | | Base Mix (g) | Add-Mix X (g) | Add-Mix Y (Sweetness) (g) | Add-Mix Z (g) |
| | | | | | Specific Base/Add-Mix Selected: | | | |
| | | | | User Selected Active Ingredient Amounts | B1 | X1 | Y1 | Z1 |
| | | | | | | Name: | | |
| | Factory ID Code | Ingredient Name (as on product label) | Category | (adjusted for purity) (g) | Berry Blast | 0 | Standard Sweetener | | TOTAL |
| 1 | A1 | ACIDULANT | Additive | — | 1.816 | — | — | — | 1.816 |
| 2 | B1 | BUFFER | Additive | — | 0.397 | — | — | — | 0.397 |
| 3 | S1 | SWEETENESS INGREDIENT X | Sweetener | — | — | — | 0.626 | — | 0.626 |
| 4 | M1 | MASKING AGENT | Flavourant | — | 0.397 | — | — | — | 0.397 |
| 5 | S2 | SALT | Flavourant | — | 0.289 | — | — | — | 0.289 |
| 6 | S3 | STABILIZER | Additive | — | 0.162 | — | — | — | 0.162 |
| 7 | A2 | ANTICAKING AGENT | Additive | — | 0.159 | — | — | — | 0.159 |
| 8 | M2 | MCT OIL | Additive | — | 0.029 | — | — | — | 0.029 |
| 9 | C1 | CREATINE | Amino Acid | 5.000 | — | — | — | — | 5.000 |
| 10 | A3 | ARGININE | Amino Acid | 1.000 | — | — | — | — | 1.000 |
| 11 | C2 | CAFFEINE | Stimulant | 0.050 | — | — | — | — | 0.050 |
| 12 | L1 | L-LEUCINE | Amino Acid | 1.500 | — | — | — | — | 1.500 |
| 13 | L2 | L-ISOLEUCINE | Amino Acid | 1.500 | — | — | — | — | 1.500 |
| 14 | L3 | L-VALINE | Amino Acid | 1.500 | — | — | — | — | 1.500 |
| Total Quantities (g): | | | | 10.550 | 3.610 | — | 0.626 | — | 14.425 |
| | | | | Water Qty (ml) | 420 | 0 | 0 | 0 | 420 |

In Table 3, the nutritional information of the blend, including protein, fats, and the like are shown for the custom nutritional supplement of the example.

TABLE 3

"Mix Info" Sheet 2
MIX INFO

| | | | MACRO NUTRIENTS (g or mg/100 g) | | | | | |
|---|---|---|---|---|---|---|---|---|
| | | | | | | | FATS | |
| | Factory ID Code | Ingredient Name (as on product label) | Energy (kJ) | PROTEIN | CARBOHYDRATES | | | Unsaturated |
| | | | | | Sugars | Complex | Total | Saturated | Mono-unsaturated |
| 1 | A1 | ACIDULANT | 13 | — | — | — | — | — | — |
| 2 | B1 | BUFFER | — | — | — | — | — | — | — |
| 3 | S1 | SWEETENESS INGREDIENT X | — | — | — | — | — | — | — |
| 4 | M1 | MASKING AGENT | — | — | — | — | — | — | — |
| 5 | S2 | SALT | — | — | — | — | — | — | — |
| 6 | S3 | STABILIZER | — | — | — | — | — | — | — |
| 7 | A2 | ANTICAKING AGENT | — | — | — | — | — | — | — |
| 8 | M2 | MCT OIL | 3700 | — | — | — | — | 92 | 6 |
| 9 | C1 | CREATINE | 1632 | 96 | — | — | — | — | — |
| 10 | A3 | ARGININE | 1632 | 96 | — | — | — | — | — |
| 11 | C2 | CAFFEINE | — | — | — | — | — | — | — |
| 12 | L1 | L-LEUCINE | 1632 | 96 | — | — | — | — | — |
| 13 | L2 | L-ISOLEUCINE | 1632 | 96 | — | — | — | — | — |
| 14 | L3 | L-VALINE | 1632 | 96 | — | — | — | — | — |

TABLE 3-continued

"Mix Info" Sheet 2
MIX INFO

MACRO NUTRIENTS (g or mg/100 g)

FATS

Unsaturated

Poly-unsaturated of wich

| ID | Omega 3 (mg) | Omega 6 (mg) | Other | Total Poly | Cis | Trans | Total Unsaturated | Total Fat | Cholesterol | Fiber |
|----|---|---|---|---|---|---|---|---|---|---|
| 1  | — | — | — | — | — | — | — | — | — | — |
| 2  | — | — | — | — | — | — | — | — | — | — |
| 3  | — | — | — | — | — | — | — | — | — | — |
| 4  | — | — | — | — | — | — | — | — | — | — |
| 5  | — | — | — | — | — | — | — | — | — | — |
| 6  | — | — | — | — | — | — | — | — | — | 100 |
| 7  | — | — | — | — | — | — | — | — | — | — |
| 8  | — | 2 | 2 | 2 | 2 | — | 8 | 100 | — | — |
| 9  | — | — | — | — | — | — | — | — | — | — |
| 10 | — | — | — | — | — | — | — | — | — | — |
| 11 | — | — | — | — | — | — | — | — | — | — |
| 12 | — | — | — | — | — | — | — | — | — | — |
| 13 | — | — | — | — | — | — | — | — | — | — |
| 14 | — | — | — | — | — | — | — | — | — | — |

Table 4 shows the vitamins and minerals thereof.

TABLE 4

"Mix Info" Sheet 3
MIX INFO

MINERALS & VITAMINS (mg/100 g)

| | | | VITAMINS | | | | | | | | | | | | | MINERALS | | | | |
|---|---|---|---|---|---|---|---|---|---|---|---|---|---|---|---|---|---|---|---|---|
| | | | | | | B | | | | | | | | | | | | | | |
| ID | Factory Code | Ingredient Name (as on product label) | A | 1 | 2 | 3 | 5 | 6 | 7 | 9 | 12 | C | D | E | K | Sodium | Potassium | Calcium | Magnesium | Phosphorous |
| 1 | A1 | ACIDULANT | — | — | — | — | — | — | — | — | — | — | — | — | — | — | — | — | — | — |
| 2 | B1 | BUFFER | — | — | — | — | — | — | — | — | — | — | — | — | — | — | 361 | — | — | — |
| 3 | S1 | SWEETENESS INGREDIENT X | — | — | — | — | — | — | — | — | — | — | — | — | — | — | — | — | — | — |
| 4 | M1 | MASKING AGENT | — | — | — | — | — | — | — | — | — | — | — | — | — | — | — | — | — | — |
| 5 | S2 | SALT | — | — | — | — | — | — | — | — | — | — | — | — | — | 394 | — | — | — | — |
| 6 | S3 | STABILIZER | — | — | — | — | — | — | — | — | — | — | — | — | — | — | — | — | — | — |
| 7 | A2 | ANTICAKING AGENT | — | — | — | — | — | — | — | — | — | — | — | — | — | — | — | — | — | — |
| 8 | M2 | MCT OIL | — | — | — | — | — | — | — | — | — | — | — | — | — | — | — | — | — | — |
| 9 | C1 | CREATINE | — | — | — | — | — | — | — | — | — | — | — | — | — | — | — | — | — | — |
| 10 | A3 | ARGININE | — | — | — | — | — | — | — | — | — | — | — | — | — | — | — | — | — | — |
| 11 | C2 | CAFFEINE | — | — | — | — | — | — | — | — | — | — | — | — | — | — | — | — | — | — |
| 12 | L1 | L-LEUCINE | — | — | — | — | — | — | — | — | — | — | — | — | — | — | — | — | — | — |
| 13 | L2 | L-ISOLEUCINE | — | — | — | — | — | — | — | — | — | — | — | — | — | — | — | — | — | — |
| 14 | L3 | L-VALINE | — | — | — | — | — | — | — | — | — | — | — | — | — | — | — | — | — | — |

The system has certain "Base Mixes" and certain "Add-Mixes" which are provided for use in the preparation of the custom nutritional supplement composition. The different Base Mixes and Add-Mixes are designed and the proportions of the different ingredients is listed as percentages i.t.o. mass. Base Mixes might consist of individual ingredients as well as Add-Mixes. The designs are shown in Table 5.

TABLE 5

"Base Mix & Add-Mix Design" Sheet
BASE MIX & ADD-MIX DESIGN

| | | | Base Mix/Add-Mix Categories: | | | | | | |
|---|---|---|---|---|---|---|---|---|---|
| | | Base Mix Category: Shakes | | | Base Mix Category: Drinks | | | Add-Mix Category X | | |
| Base Mix/Add-Mix ID: | | A1 | A2 | A3 | B1 | B2 | B3 | X1 | X2 | X3 |
| Base Mix/Add-Mix Adding Factor: | | 1 | | | 0.95 | | | 1 | | |
| Name: | | Standard Base Mix | Shake 2 | Shake 3 | Berry Blast | Drink 2 | Drink 3 | Standard Add-Mix X | Add-Mix X2 | Add-Mix X3 |
| Minimum Qty (g): | | 27 | 28 | 20 | 2.26 | 2.1 | 2.5 | 0.01 | 0.00 | 0.00 |
| Water/Milk Ratio (ml/g): | | 8.3 | 7.2 | 10.1 | 115.38 | 120 | 150 | N.A. for this example | | |
| Total Allocated | | 100% | 100% | 100% | 100% | 100% | 100% | 100% | 100% | 100% |
| Ingredient ID (% by Mass) | X Add-Mix Category X | | | | | | | N.A. for this example | | |
| | Y Add-Mix Category Y (Sweetness) | | | | 10.0% | | | | | |
| | Z Add-Mix Category Z | | | | | | | | | |
| | 1 ACIDULANT | | | | 50.3% | | | | | |
| | 2 BUFFER | | | | 11.0% | | | | | |
| | 3 SWEETNESS INGREDIENT X | | | | 0.0% | | | | | |
| | 4 MASKING AGENT | | | | 11.0% | | | | | |
| | 5 SALT | | | | 8.0% | | | | | |
| | 6 STABILIZER | | | | 4.5% | | | | | |
| | 7 ANTICAKING AGENT | | | | 4.4% | | | | | |
| | 8 MCT OIL | | | | 0.8% | | | | | |
| | 9 CREATINE | | | | | | | | | |
| | 10 ARGININE | | | | | | | | | |
| | 11 CAFFEINE | | | | | | | | | |
| | 12 L-LEUCINE | | | | | | | | | |
| | 13 L-ISOLEUCINE | | | | | | | | | |
| | 14 L-VALINE | | | | | | | | | |
| | 15 STEVIA | | | | | | | | | |
| | 16 XYLITOL | | | | | | | | | |

| | | Base Mix/Add-Mix Categories: | | | | | |
|---|---|---|---|---|---|---|---|
| | | Add-Mix Category Y (Sweetness) | | | Add-Mix Category Z | | |
| Base Mix/Add-Mix ID: | | Y1 | Y2 | Y3 | Z1 | Z2 | Z3 |
| Base Mix/Add-Mix Adding Factor: | | 1.0 | 118.0 | 0.9 | 1 | | |
| Name: | | Standard Sweetener | Xylitol | Stevia | Standard Add-Mix Z | Add-Mix Z2 | Add-Mix Z3 |
| Minimum Qty (g): | | 0.00 | 1.00 | 0.01 | 0.00 | 0.00 | 0.00 |
| Water/Milk Ratio (ml/g): | | N.A. for this example | | | | | |
| Total Allocated | | 100% | 100% | 100% | 100% | 100% | 100% |
| Ingredient ID (% by Mass) | X Add-Mix Category X | N.A. for this example | | | | | |
| | Y Add-Mix Category Y (Sweetness) | | | | | | |
| | Z Add-Mix Category Z | | | | | | |
| | 1 ACIDULANT | | | | | | |
| | 2 BUFFER | | | | | | |
| | 3 SWEETNESS INGREDIENT X | 100% | | | | | |
| | 4 MASKING AGENT | | | | | | |
| | 5 SALT | | | | | | |
| | 6 STABILIZER | | | | | | |
| | 7 ANTICAKING AGENT | | | | | | |
| | 8 MCT OIL | | | | | | |
| | 9 CREATINE | | | | | | |
| | 10 ARGININE | | | | | | |
| | 11 CAFFEINE | | | | | | |
| | 12 L-LEUCINE | | | | | | |
| | 13 L-ISOLEUCINE | | | | | | |
| | 14 L-VALINE | | | | | | |
| | 15 STEVIA | | | 100% | | | |
| | 16 XYLITOL | | 100% | | | | |

NB. Table is truncated for this example and typically continues downwards

Minimum quantities of base mix are defined and ratio of water/milk is stated.

The final proportions of active ingredients, Add-Mixes and Base Mixes is automatically determined by using pre-determined "Base Mix Factors" (attribute assigned to an Active Ingredient), "AddMix Factors" (attribute assigned to an Active Ingredient) and "Base Mix Adding Factors" (attribute assigned to a Base Mix), and "Add-Mix Adding Factors" (attribute assigned to an Add-Mix). A typical method for determining these factors is described below.

For each ingredient a Base Mix Factor is determined. A proposed empirical method is to prepare a Base Mix complete with water added (one of the Base Mixes are chosen as the standard Base Mix). An ingredient is then tested by incrementally adding more of it and tasting/testing it to determine the maximum amount which can be added before the mix becomes unacceptable. The Base Mix Factor would then be the inverse of this ingredient—Base Mix ratio and is recorded on the "Ingredient information & Properties" sheet, Table 6.

based on the concentrations of hydrogen ions. Another example is relationships mined from data by means of machine learning and artificial intelligence to determine Add-Mix Factors and to refine the correlation algorithms.

Add-Mix Factors should only be calculated for the standard Add-Mix (X1, Y1 or Z1), the Add-Mix Adding Factors

TABLE 6

"Ingredient Information & Properties" Sheet
INGREDIENT INFORMATION & PROPERTIES

| ID | Factory Code | Ingredient Name (as on product label) | Category | Specifiable by User? | Permissible Range (grams) | | |
|---|---|---|---|---|---|---|---|
| | | | | | Min | Recommended | Max |
| 1 | A1 | ACIDULANT | Additive | No | | | |
| 2 | B1 | BUFFER | Additive | No | | | |
| 3 | S1 | SWEETENESS INGREDIENT X | Sweetener | No | | | |
| 4 | M1 | MASKING AGENT | Flavourant | No | | | |
| 5 | S2 | SALT | Flavourant | No | | | |
| 6 | S3 | STABILIZER | Additive | No | | | |
| 7 | A2 | ANTICAKING AGENT | Additive | No | | | |
| 8 | M2 | MCT OIL | Additive | No | | | |
| 9 | C1 | CREATINE | Amino Acid | Yes | 0.100 g | 2.500 g | 10.000 g |
| 10 | A3 | ARGININE | Amino Acid | Yes | 0.100 g | 1.000 g | 5.000 g |
| 11 | C2 | CAFFEINE | Stimulant | Yes | 0.020 g | 0.050 g | 0.100 g |
| 12 | L1 | L-LEUCINE | Amino Acid | Yes | 0.100 g | 1.500 g | 5.000 g |
| 13 | L2 | L-ISOLEUCINE | Amino Acid | Yes | 0.100 g | 1.500 g | 5.000 g |
| 14 | L3 | L-VALINE | Amino Acid | Yes | 0.100 g | 1.500 g | 5.000 g |
| 15 | S2 | STEVIA | Sweetener | No | | | |
| 16 | S3 | XYLITOL | Sweetener | No | | | |

| ID | Base Mix Factor (Category: Shakes) (grams std base mix/grams active) | Base Mix Factor (Category: Drinks) (grams std base mix/grams active) | Add-Mix Factor (Category X) (miligrams std add-mix/grams active) | Add-Mix Factor (Category Y (Sweetness)) (miligrams std add-mix/grams active) | Add-Mix Factor (Category Z) (miligrams std add-mix/grams active) |
|---|---|---|---|---|---|
| 1 | | | | | |
| 2 | | | | | |
| 3 | | | | | |
| 4 | | | | | |
| 5 | | | | | |
| 6 | | | | | |
| 7 | | | | | |
| 8 | | | | | |
| 9 | 12 | 0.12 | | | |
| 10 | 3 | 0.2 | | | |
| 11 | 150 | 15 | | | |
| 12 | 6 | 0.5 | | 50 | |
| 13 | 7 | 0.5 | | 50 | |
| 14 | 5 | 0.5 | | 50 | |
| 15 | | | | | |
| 16 | | | | | |

NB. Table is truncated for this example and typically continues downwards

If the test mix becomes unacceptable due to a characteristic which can more effectively remedied by the addition of a specific counter agent instead of just adding more of the Base Mix, an "Add-Mix" is designed. An example is a sour ingredient which will require a sweetening agent as neutraliser. The ingredient composition of this Add-Mix is captured on the "Base Mix Design" sheet.

The most effective ratio of active ingredient vs specific Add-Mix might be empirically determined by mixing an amount of the active ingredient in water and then adding Add-Mix until the specific property is sufficiently neutralised (often, the more the Add-Mix the less Base Mix required, it might thus be a balance). The proportion of Add-Mix to active ingredient is then recorded as the Add-Mix Factor on the "Ingredient Info" sheet. An example of a theoretically determined factor would be when an acidic Active Ingredient is neutralised with a theoretically calculated amount of pH increasing additive (as an Add-Mix)

are used to account for the different Add-Mixes within the same Add-Mix Category which are designed for the same purpose and might thus be used interchangeably eg. stevia mix vs xylitol mix as alternative Add-Mixes within the sweetening Add-Mix Category. The choice of which specific Add-Mix to use within an Add-Mix category is typically user selected.

The active ingredient is then mixed with the Add-Aix and the steps are repeated with this mixture to determine the active's Base Mix Factor, to be recorded on the "Ingredient Information & Properties" sheet.

A standard active testing mix is chosen from +−5 popular active ingredients (eg. Every ingredient at recommended dose multiplied by 10), the neutralising Add-Mixes should be included at the specified rates (summation of ingredient mass multiplied by Add-Mix Factor).). Base Mix is then incrementally added until the product is satisfactory. The Base Mix Adding Factor of the Base Mix is then adjusted on the "Base Mix Design" sheet (the sweetener factors should be returned to the correct value) until the amount of base mix specified on the "Mix Info" sheet is the same as the amount empirically tested.

The Add-Mix Adding Factors for the standard Add-Mixes (X1, Y1 and Z1) are typically equal to 1. Additional Add-Mixes within the same Add-Mix Category should then be tested and its adding factor adjusted to a % of the standard Add-Mix. (eg. a sweetness Add-Mix's sweetness should be compared with the standard sweetness Add-Mix to determine the relationship: eg. 5% Add-Mix Adding Factor would then mean that either 100 mg of Add-Mix Y1 or 5 mg of the new sweetness Add-Mix can be used interchangeably with the same result).

Provision is made for the sweetener portion (or any other portion) to be removed from the Base Mix recipes, and added as an Add-Mix, to allow for the specification of different options (eg stevia vs sucralose) without multiplying the number of base mixes required. For this purpose the % portion of standard sweetener (Add-Mix Y1) (or any other Add-Mix representing a portion of the Base Mix) is specified instead of the individual ingredients in the Base Mix itself. The ingredient quantities should only be in the Add-Mix design. See Table 5: "Base Mix & Add-Mix Design" Sheet for an example.

Figure 1:
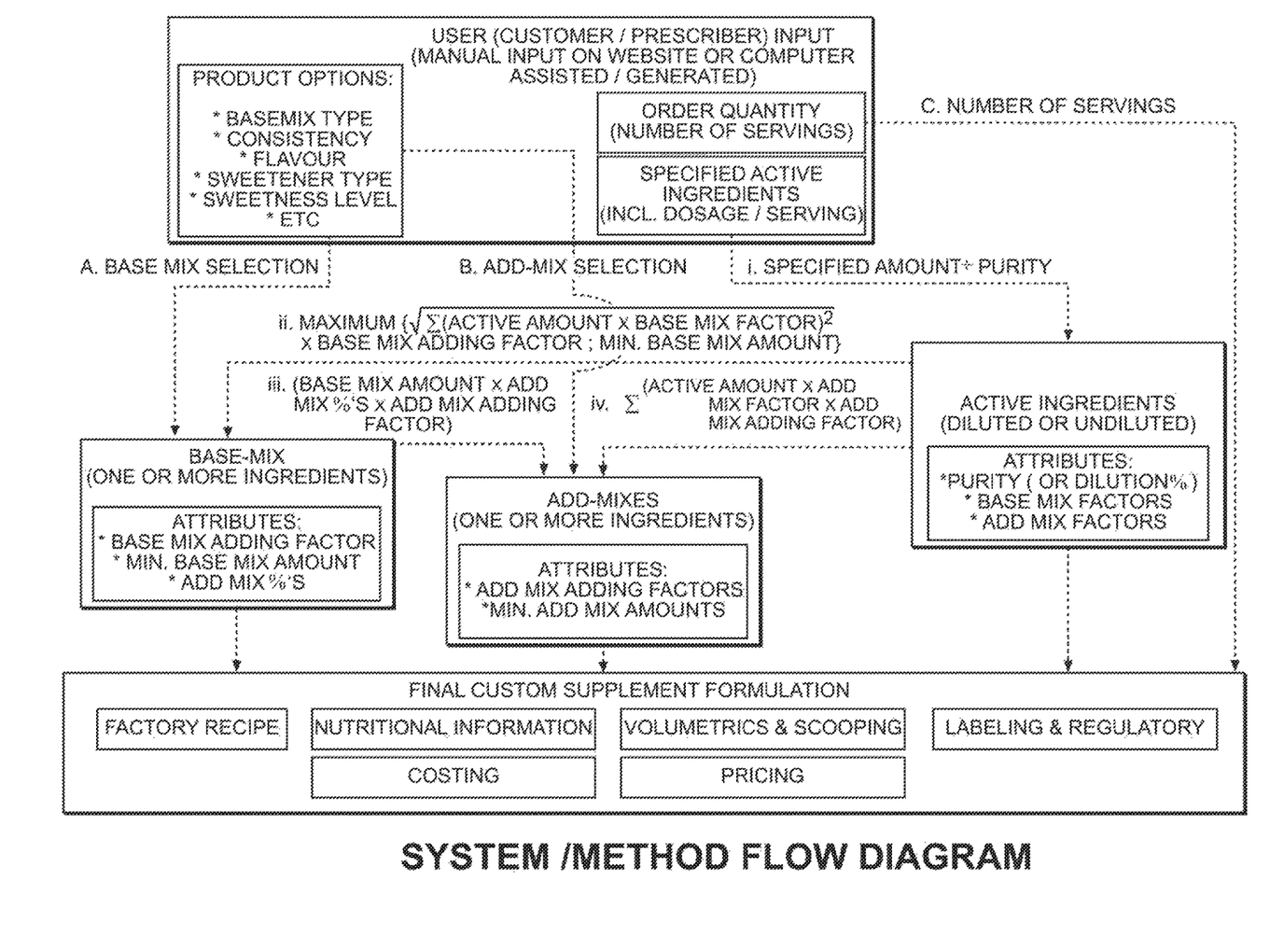

Thus, one proposed automatic methodology of preparing a custom nutritional supplement composition of the example is as follows and which is illustrated by the diagram in FIG. 1: System/Method Flow Diagram. (note that the verbs refer to actions automatically performed by the computer system)

1. The specifically added Active Ingredient quantities selected by the customer by means of the user interface (http://www.tailorblend.co.za/Web/Blend), are read from the "Mixing Input" sheet and added in the "Mix Info" sheet after adjusting for the purity (or dilution) of each ingredient in its powder form. (FIG. 1: calculation i.)
2. The ingredients in the Base Mix (as specified in "Mixing Inputs" sheet) are added in the ratios as specified in the "Base Mix Design" sheet and at quantities determined as follows: each Active Ingredient quantity is multiplied with its Base Mix Factor and multiplied with the Base Mix Adding Factor to determine the contribution the specific Active Ingredient makes to the total Base Mix quantity. The contributions of all the Active Ingredients are then aggregated (using the "root of the sum of squares" function) and compared to the minimum Add-Mix quantity, the largest of which is chosen. (FIG. 1: calculation ii.)
3. The ingredients in the Add-Mixes (as specified in "Mixing Inputs" sheet) are added according to each Active Ingredient quantity multiplied with the Add-Mix Factor (ingredient attribute) multiplied with the Add-Mix Adding Factor (Add-Mix attribute) for each Add-Mix. (FIG. 1: calculation iv.)
4. In addition to its function as neutralising agent, additional amounts of Add-Mix (eg. sweetening Add-Mix) might be added as a function of the amount of Add-Mix forming part of the Base-Mix. The Base Mix amount is thus multiplier by the Add Mix % and multiplied by the Add-Mix Adding Factor. (FIG. 1: calculation iii.)
5. The quantity of each ingredient is calculated by aggregating all the amounts calculated for each specific function of the ingredient (i.e. Active Ingredient (user specified)+Base Mix+Add-Mixes (added due to specific Active Ingredients)+Add-Mix (as a part of the Base Mix (substitute for specific ingredients)). All the attributes of each ingredient at its calculated quantity are then collected from the ingredient specific "Ingredient Info" sheet, including its nutritional information, cost etc. and aggregated in the blend specific "Mix Info" sheet (Tables 2 to 4).
6. The quantity of liquid to be added to the powder to reach the optimal final state of the product is calculated by multiplying the base mix quantity with the "water/milk ratio" as specified on the "Base Mix Design" sheet (Table 5).
7. A recipe, which is used to manufacture the blend, is generated from the information in the "Mix Info" sheet (Tables 2 to 4).
8. The density and the angle of repose of the final blend is calculated from the measurement of the weight of a level and a heaped scoop of the blended powder during the manufacturing process. The masses of the different available scoop combinations, using the available scoop sizes and different configurations eg. level scoop or heaped scoop, are calculated. The "scooping" (recommended volumetric serving size, displayed on the product label) is determined by comparing the ideal mass of a serving ("Mix Info" sheet) with that of the available scoop combinations and selecting the nearest one.
9. The product label is populated with the information from the "Mix Info" sheet and peripheral information derived thereof, including; the scooping, warning messages, usage instructions etc.

It should be understood that the specific sequence of steps 1 to 9 above is not intended to be limited to these 9 steps and their order as illustrated.

It is believed to be an advantage of the invention as illustrated by the example that a customer can select the amounts of the active ingredient's he or she requires, within predetermined minimum and maximum parameters, and the system selects the required additives at the required quantities to make the custom nutritional supplement composition which is palatable as well as having the desired nutritional characteristics, in an automated or semi-automated manner.

The invention claimed is:

1. A computerized system implementing a method of altering the flavour, stability, consistency, texture and colour of a custom nutritional supplement composition containing nutritional supplement ingredients selected by a user of the system, said method including:
   a) determining one or more quantitative relationships between a plurality of active ingredients, a plurality of user-specifiable organoleptic qualities, and a plurality of additive ingredients that define ratios of ingredients included in an organoleptically optimal nutritional supplement relative to one another, wherein organoleptic qualities include a flavour, a stability, a consistency, a texture, and a colour of a custom nutritional supplement;
   b) codifying the one or more quantitative relationships in an executable algorithm as mathematical constants, wherein the algorithm calculates quantities of ingredients included in the custom nutritional supplement, and wherein the constants include one or more of the following: 'BaseMix Factor', 'AddMix Factor', 'BaseMix Adding Factor' and/or 'AddMix Adding Factor';
   c) providing within a user interface data of user selectable ingredients and qualities and having the user interface with the data via the user interface and select from the selectable ingredients and qualities to provide a desired supplement profile, wherein the desired supplement profile includes data of: one or more selected active ingredients and one or more user-specified organoleptic qualities;

d) inputting the user selected data of the desired supplemental profile into the algorithm to automatically determine a custom nutritional supplement recipe;

e) selecting one or more components to be included in a custom nutritional supplement based on the custom nutritional supplement recipe, wherein the one or more components include one or more of: one or more additive ingredients, the one or more selected active ingredients, one or more Base Mixes, and one or more Add Mixes; and f) manufacturing the custom nutritional supplement by combining the one or more selected components in quantities defined by the custom nutritional supplement recipe.

2. A system as claimed in claim 1, which includes a computer system including a user interface whereby the user submits data signifying their selection of nutritional supplement composition ingredients, their selection of quantities per serving or ratios, their preferred flavour, and their selection of additive type preferences, which data is processed on a CPU of the computer system and the additive data relevant to the custom nutritional supplement composition is automatically calculated by means of the algorithm, which is executed by the CPU, using data retrieved from a data storage on the computer system and dependent on data signifying the user selected parameters.

3. A system as claimed in claim 1, wherein the method of the system pertains to the way in which the combination and quantities of the additives are determined, making it possible to automate the formulation and production of a custom nutritional supplement composition product, with desired flavour, and texture and other sensory characteristics.

4. A system as claimed claim 1, wherein the method provides for the automatic formulation of a final recipe for a nutritional powder supplement, based on the criteria specified by the user, who may be the prescriber or consumer thereof, the criteria including specified quantities of nutritional ingredients and/or macro nutrients and/or a flavour option and/or an additive type option chosen from a catalogue detailing the available options and quantity ranges.

5. A system as claimed in claim 4, wherein the catalogue is displayed on a website in communication with the computer system.

6. A system as claimed in claim 1, wherein the method entails the automatic specification of additives, additional to the combination of nutritional ingredients, macro nutrients, and the like, necessary to satisfy the user's nutritional requirements, with the purpose of creating a final recipe that will ensure the palatability, stability, consistency, texture and colour of the product in its final form before ingestion, wherein the additives are selected from colourant, stabiliser, thickener, flavouring, sweetener, anti-foaming agents, and preservatives.

7. A system as claimed in claim 6, wherein the correlation of the data in respect of the combination of additives required, and their quantities, is based on theoretically and empirically determined relationships of these substances with each offered nutritional ingredient and their combinations and with the additives themselves, in the determination of the final product's sensory properties.

8. A system as claimed in claim 7, wherein data in respect of these relationships is predetermined and stored on the computer system to permit retrieval thereof thereby to allow the computer assisted automatic formulation of the final recipe once the input criteria are specified.

9. A system as claimed in claim 1, wherein the method further includes an automatic procedure to determine the serving size, including volume and mass, necessary to meet the specified criteria as well as the adjustment of the recipe to allow the use of standard serving sizes, if required.

10. An automated method of preparing a custom nutritional supplement composition, said method including:

determining one or more quantitative relationships between a plurality of active ingredients, a plurality of user-specifiable organoleptic qualities, and a plurality of additive ingredients that define ratios of ingredients included in an organoleptically optimal nutritional supplement relative to one another, wherein organoleptic qualities include a flavour, a stability, a consistency, a texture, and a colour of a custom nutritional supplement;

preparing one or more master batches of one or more Base Mixes and one or more Add Mixes including one or more nutritional supplement ingredients and/or one or more additives based on the one or more quantitative relationships;

codifying the one or more quantitative relationships in an executable algorithm as mathematical constants, wherein the algorithm calculates quantities of ingredients included in the custom nutritional supplement, and wherein the constants include one or more of the following: 'BaseMix Factor', 'AddMix Factor', 'BaseMix Adding Factor' and/or 'AddMix Adding Factor';

providing within a user interface data of user selectable ingredients and qualities and having the user interface with the data via the user interface and select from the selectable ingredients and qualities to provide a desired supplement profile, wherein the desired supplement profile includes data of: one or more selected active ingredients and one or more user-specified organoleptic qualities;

inputting the user selected data of the desired supplemental profile into the algorithm to automatically determine a custom nutritional supplement recipe;

selecting one or more components to be included in a custom nutritional supplement based on the custom nutritional supplement recipe, wherein the one or more components include one or more of: one or more additive ingredients, the one or more selected active ingredients, one or more Base Mixes, and one or more Add Mixes; and manufacturing the custom nutritional supplement by combining the one or more selected components in quantities defined by the custom nutritional supplement recipe thereby obtaining a palatable, stabilised, custom nutritional supplement product having a desired flavour, colour and consistency, or any other sensory characteristics, while reducing a number of components required to be blended to achieve same.

11. An automated method as claimed in claim 10, wherein the master batches include one or more nutritional ingredients which are used in a number of custom nutritional supplement compositions, so that the number of individual ingredients which need to be handled and blended in the production of the product is reduced.

12. An automated method as claimed in claim 11, wherein the nutritional ingredients are premixed in preselected ratios.

13. An automated method as claimed in claim 10, wherein the master batches include one or more additives selected from colourant, stabiliser, thickener, flavouring, sweetener, anti-foaming agents, and preservatives.

14. An automated method as claimed in claim 10, wherein the master batches are prepared in advance in large quantities and stored in bulk storage, whereas the individual ingredients and additives which may be blended with the master batches are stored in smaller quantities.

15. An automated method as claimed in claim 10, wherein the blending of the custom nutritional supplement product is automated at least to the extent of determining and dispensing the master batches required for a particular custom nutritional supplement composition product.

16. An automated method as claimed in claim 15, wherein the automated method includes the automated determination and dispensing of individual additives and nutritional ingredients required in addition to the master batches.

* * * * *